(12) United States Patent
Osterberg

(10) Patent No.: US 7,814,913 B2
(45) Date of Patent: *Oct. 19, 2010

(54) CONDOM

(76) Inventor: Brian Osterberg, P.O. Box 42, Petoskey, MI (US) 49770

( * ) Notice: Subject to any disclaimer, the term of this patent is extended or adjusted under 35 U.S.C. 154(b) by 159 days.

This patent is subject to a terminal disclaimer.

(21) Appl. No.: 11/530,779

(22) Filed: Sep. 11, 2006

(65) Prior Publication Data
US 2007/0017528 A1    Jan. 25, 2007

Related U.S. Application Data

(63) Continuation-in-part of application No. 11/064,590, filed on Feb. 24, 2005, now Pat. No. 7,392,807.

(60) Provisional application No. 60/547,403, filed on Feb. 24, 2004.

(51) Int. Cl.
A61F 6/06    (2006.01)
(52) U.S. Cl. .................. 128/830; 128/918
(58) Field of Classification Search .......... 128/832, 128/844, 842, 902
See application file for complete search history.

(56) References Cited

U.S. PATENT DOCUMENTS

| 4,735,621 A | 4/1988 | Hessel et al. | |
| 4,834,113 A | 5/1989 | Reddy | |
| 4,840,624 A | 6/1989 | Lee | |
| 4,869,723 A * | 9/1989 | Harmon | 604/349 |
| 4,993,433 A | 2/1991 | Reddy | |
| 5,094,250 A | 3/1992 | Hessel et al. | |
| 5,168,881 A | 12/1992 | Reddy | |
| 5,269,320 A * | 12/1993 | Hunnicutt | 128/830 |
| 5,325,871 A * | 7/1994 | Reddy | 128/830 |
| 5,377,692 A | 1/1995 | Pfeil | |
| 5,413,117 A | 5/1995 | Wills | |
| 5,490,519 A | 2/1996 | Hessel et al. | |
| 5,490,525 A | 2/1996 | Reddy | |
| 5,515,862 A | 5/1996 | Artsi et al. | |
| 5,535,757 A | 7/1996 | Fleming, Jr. | |
| 5,638,829 A | 6/1997 | Najor | |
| 5,749,862 A | 5/1998 | Lau et al. | |
| 5,992,415 A * | 11/1999 | Alla et al. | 128/830 |
| 6,651,667 B2 * | 11/2003 | Osterberg | 128/844 |
| 7,322,358 B2 * | 1/2008 | Tam et al. | 128/830 |
| 7,392,807 B2 * | 7/2008 | Osterberg | 128/830 |

(Continued)

FOREIGN PATENT DOCUMENTS

DE    3644344    7/1988

(Continued)

Primary Examiner—Patricia Bianco
Assistant Examiner—Camtu T Nguyen
(74) Attorney, Agent, or Firm—Gifford, Krass, Sprinkle, Anderson & Citkowski, P.C.

(57) ABSTRACT

A condom may include pouch having a wall and a frame. The pouch may have an open end and a closed end and the frame may be positioned proximate the open end. An anchoring device may be secured to the pouch proximate the closed end. Further, a harness or accessory attachment may be provided to assist in securing the condom to a user. At least one condom accessory, for stimulating at least one of the five senses, may also be positioned on or in at least one of the pouch, frame, anchor or harness using a variety of attachment methods.

8 Claims, 9 Drawing Sheets

U.S. PATENT DOCUMENTS

2004/0133070 A1  7/2004  Lin

FOREIGN PATENT DOCUMENTS

| | | |
|---|---|---|
| DE | 29607317 | 8/1997 |
| EP | 0552814 A1 | 7/1993 |
| EP | 0965314 A1 | 12/1999 |
| GB | 2289224 | 11/1995 |
| JP | 63234968 A2 | 9/1988 |
| JP | 6417225 | 1/1989 |
| JP | 03007151 | 1/1991 |
| WO | WO-8805291 | 7/1988 |
| WO | WO-9829062 A1 | 7/1998 |

* cited by examiner

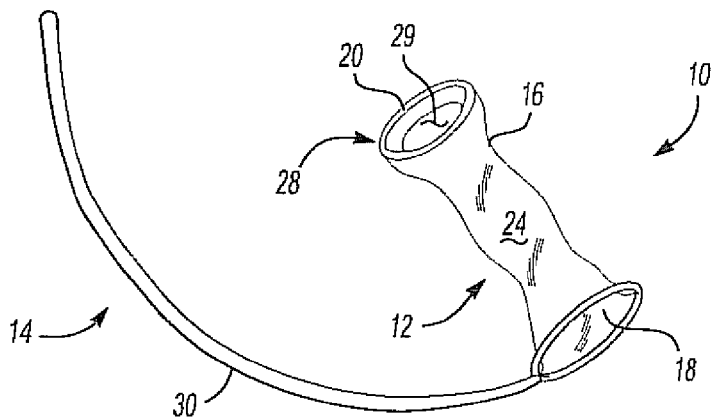
Fig-1
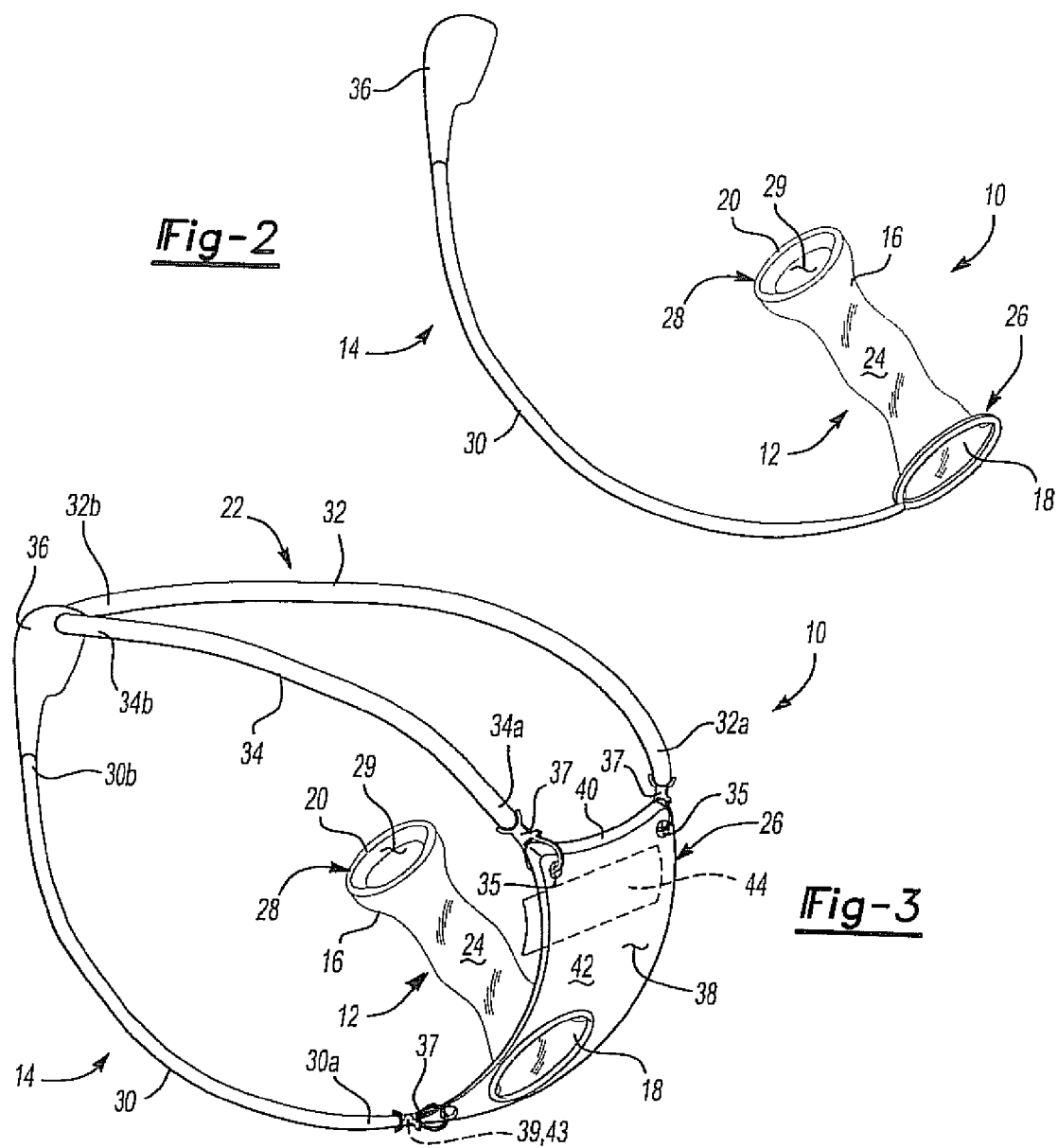
Fig-2
Fig-3

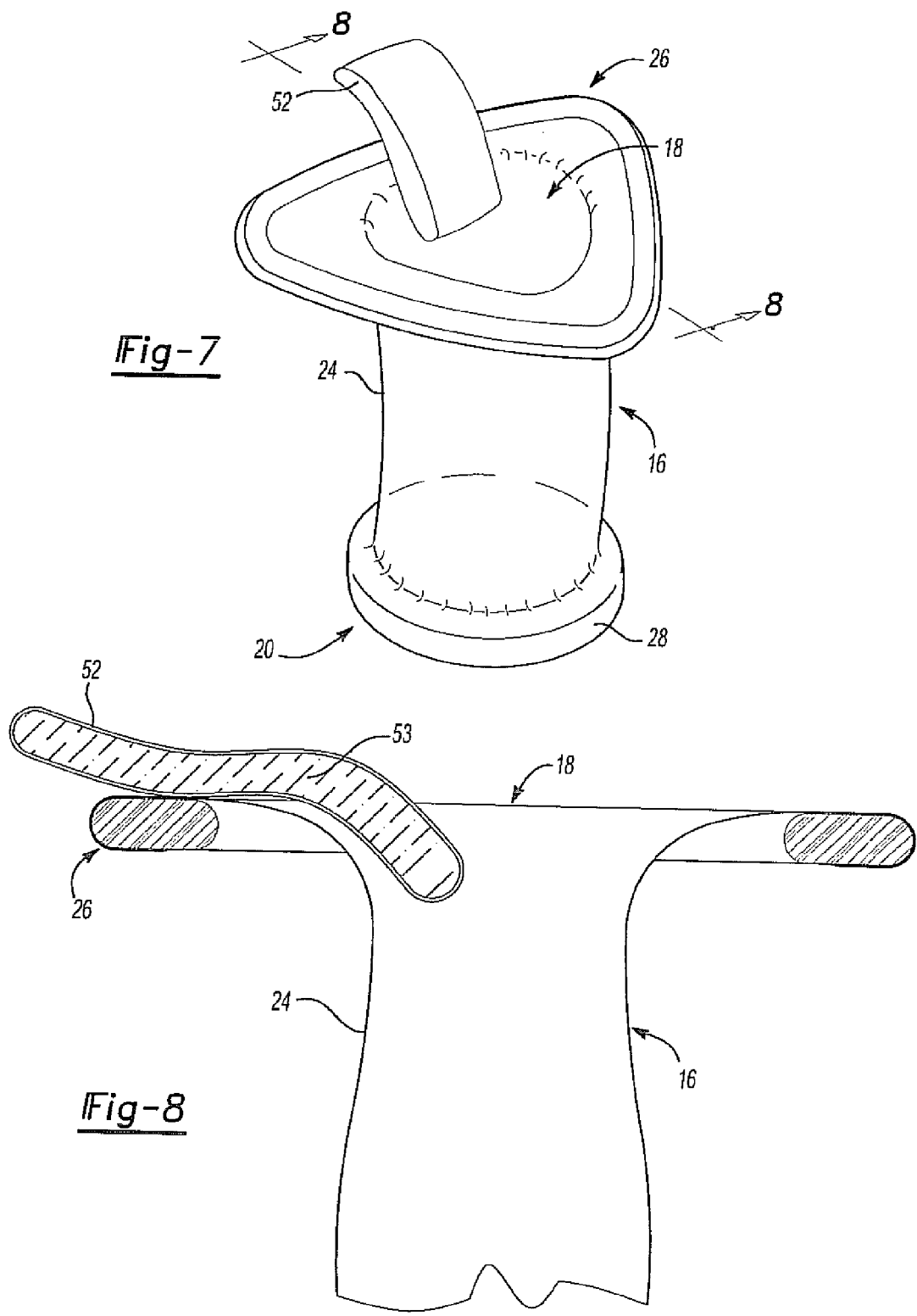

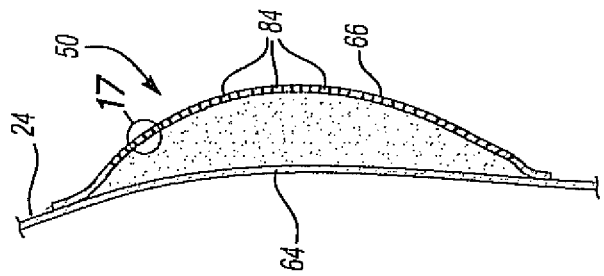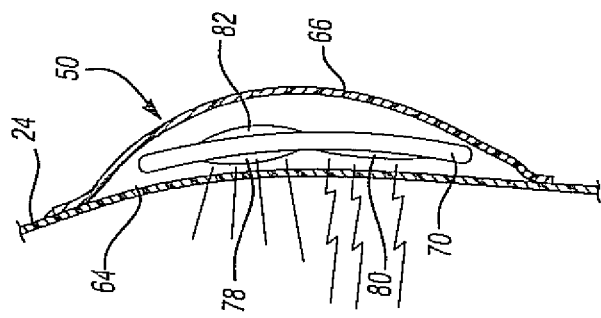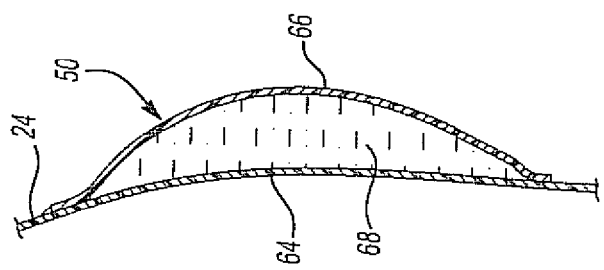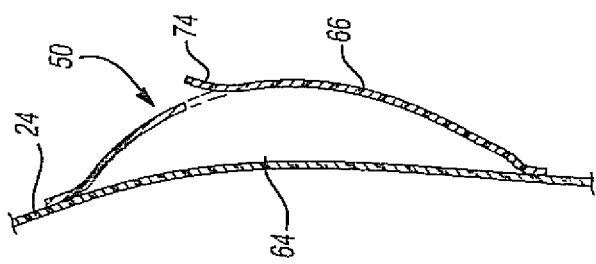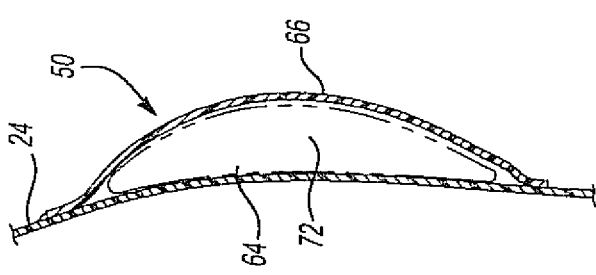

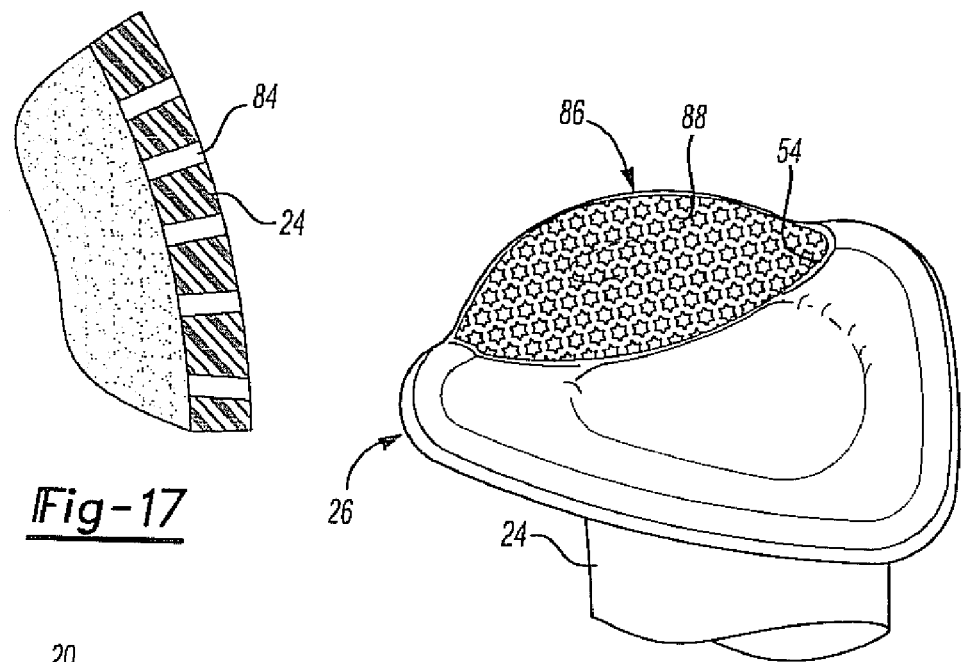
Fig-17
Fig-18
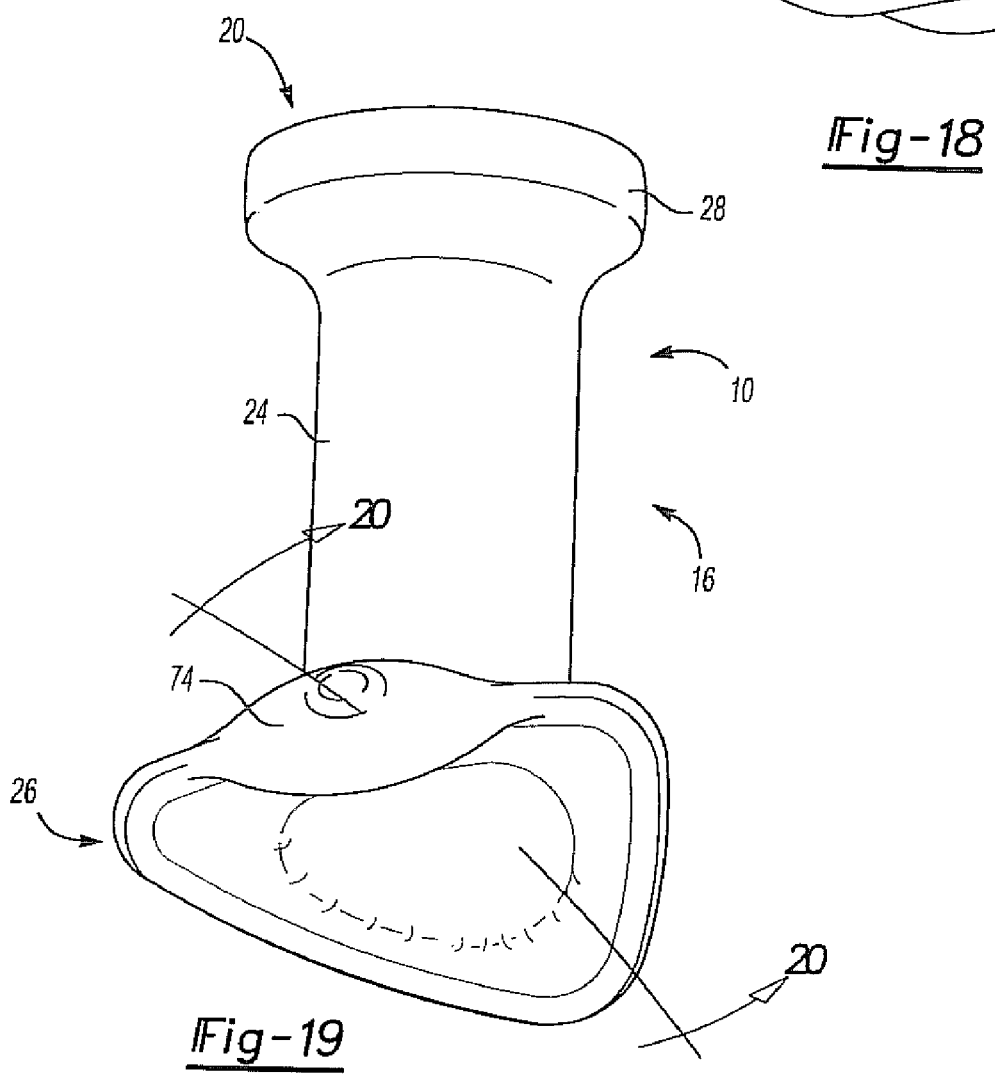
Fig-19

CONDOM

CROSS-REFERENCE TO RELATED APPLICATIONS

This application is a continuation-in-part of pending U.S. patent application Ser. No. 11/064,590, filed Feb. 24, 2005, which claims priority from U.S. provisional patent application No. 60/547,403, filed Feb. 24, 2004.

BACKGROUND OF THE INVENTION

1. Field of the Invention

The present invention concerns an improved condom. More particularly, the invention concerns a condom that may include a condom accessory. The condom may also include a resilient strap and/or a harness/G-string type assembly.

2. Reference to Related Art

Disclosed in the prior art are a variety of condoms having a G-string or similar harness assembly for use in securing a condom to the user. For example, International Publication No. WO 88/05291 disclosed a barrier device that included a continuous impermeable shield member shaped and dimensioned so that, in operation, it covered the entrance of a user's vagina. Integral with the shield member may be a continuous, impermeable, flexible pouch arranged to receive a penis and to be introduced into a vagina to form a liquid barrier between the penis and vagina. The shield and pouch may be secured in an operational position by straps that pass around the hips and between the buttocks to form a G-string type garment. Alternatively, the membrane may be secured in the operational position in a panty-like garment.

In another example, U.S. Pat. No. 5,168,881 (see also 5,490,525) to Reddy discussed a prophylactic device. The device included a hollow pouch that had a closed end and an open end. The open end of the pouch may be attached to and surrounded by a continuous flange member. The flange extends outwardly at least one inch around the open end of the pouch. The flange must be liquid impermeable and may be flexible or nonflexible and elastic or non-elastic. A plurality of straps are secured to the flange that are connected at their opposite ends to bands that may be worn around the waist or around the pelvic region of the female person using the device. In another embodiment, the device may be connected to a bikini-like panty garment having an elastic waist portion.

SUMMARY OF THE INVENTION

A condom may include pouch having a wall and a frame. The pouch may have an open end and a closed end and the frame may be positioned proximate the open end. An anchoring device may be secured to the pouch proximate the closed end. Further, a harness may be optionally provided to assist in securing the condom to a user. At least one condom accessory, for stimulating at least one of the five senses, may also be positioned on or in at least one of the pouch, frame, anchor or harness using a variety of attachment methods.

For example, the condom may include a pouch that has a wall that defines an open end, a closed end. A frame may also be provided proximate the open end. Specifically, if present, the frame may be positioned proximate the open end of the pouch and constructed so that it extends around a perimeter or a portion of the perimeter of the open end.

An anchoring device, such as a flexible disc may be positioned within the pouch proximate the closed end or at any point along on the wall of the condom pouch 16. In operation, when the pouch is inserted in a user's vagina, the anchoring device may cause the wall of the pouch to press against the vaginal wall and thereby reduce the possibly of accidental removal of the pouch during use.

A harness may be provided that includes a resilient center strap and may include a resilient first side strap and a resilient second side strap. Each of the straps may have a first end secured to the closed end (or the frame) of the pouch and a second end opposite the first end that are secured together.

In operation (when the harness is used), at least the center strap may extend from the open end of the pouch, between the legs and buttocks of the user to resiliently engage the user's back. As such, the strap aids in securing the pouch in position during use.

As mentioned, the condom assembly may also include a condom accessory that may be positioned on or in the condom wall, on or in the anchor, positioned in a pocket or space defined in the wall or positioned on the frame of the condom or any part of the harness, etc. The condom accessory may include, for example, a vibration (or oscillation) device, a light and/or sound device, a lubricating fluid, a scented fluid, a pillow, a solid device, or a pad and any combination thereof. One or more than one condom accessory may be used on the condom, depending on the model and/or the needs of the user. The condom accessories may be constructed to be deposable or reusable. Furthermore, the condom may be constructed so that the user may interchange the condom accessories to meet his or her needs.

BRIEF DESCRIPTION OF THE DRAWINGS

Reference will now be made to the attached drawings wherein like reference numbers refer to like parts throughout and wherein:

FIG. 1 is a perspective view of the improved condom of the present invention;

FIG. 2 is a perspective view of another embodiment of the improved condom of the present invention;

FIG. 3 is a perspective view of yet another embodiment of the improved condom of the present invention including a flange and eyelets;

FIG. 7 is a perspective view of an embodiment of an improved condom having a pillow positioned on the frame of the condom;

FIG. 8 is planar side view of the embodiment of an improved condom shown in FIG. 7;

FIGS. 12 is a partial planar side view showing a condom accessory positioned within the space or pocket;

FIG. 13 is a partial planar side view showing the space or pocket including an opening to permit the insertion of a condom accessory;

FIG. 14 is a partial planar side view showing the space or pocket containing a fluid or gel condom accessory;

FIG. 15 is a partial planar side view showing the space or pocket containing a light and/or sound generating condom accessory;

FIG. 16 is a partial planar side view showing the space or pocket having at least one micro-aperture;

FIG. 17 is an enlarged partial planar side of the cavity or pillow of FIG. 16 showing a plurality of micro-apertures defined in the space or pocket;

FIG. 18 is a perspective view of the embodiment of an improved condom showing the space or pocket constructed as part of the frame of the condom and wherein the cavity or pillow includes an open lattice construction;

FIG. 19 is a perspective view of the embodiment of an improved condom showing the space or pocket constructed as part of the frame of the condom.

DETAILED DESCRIPTION

Figure 4:
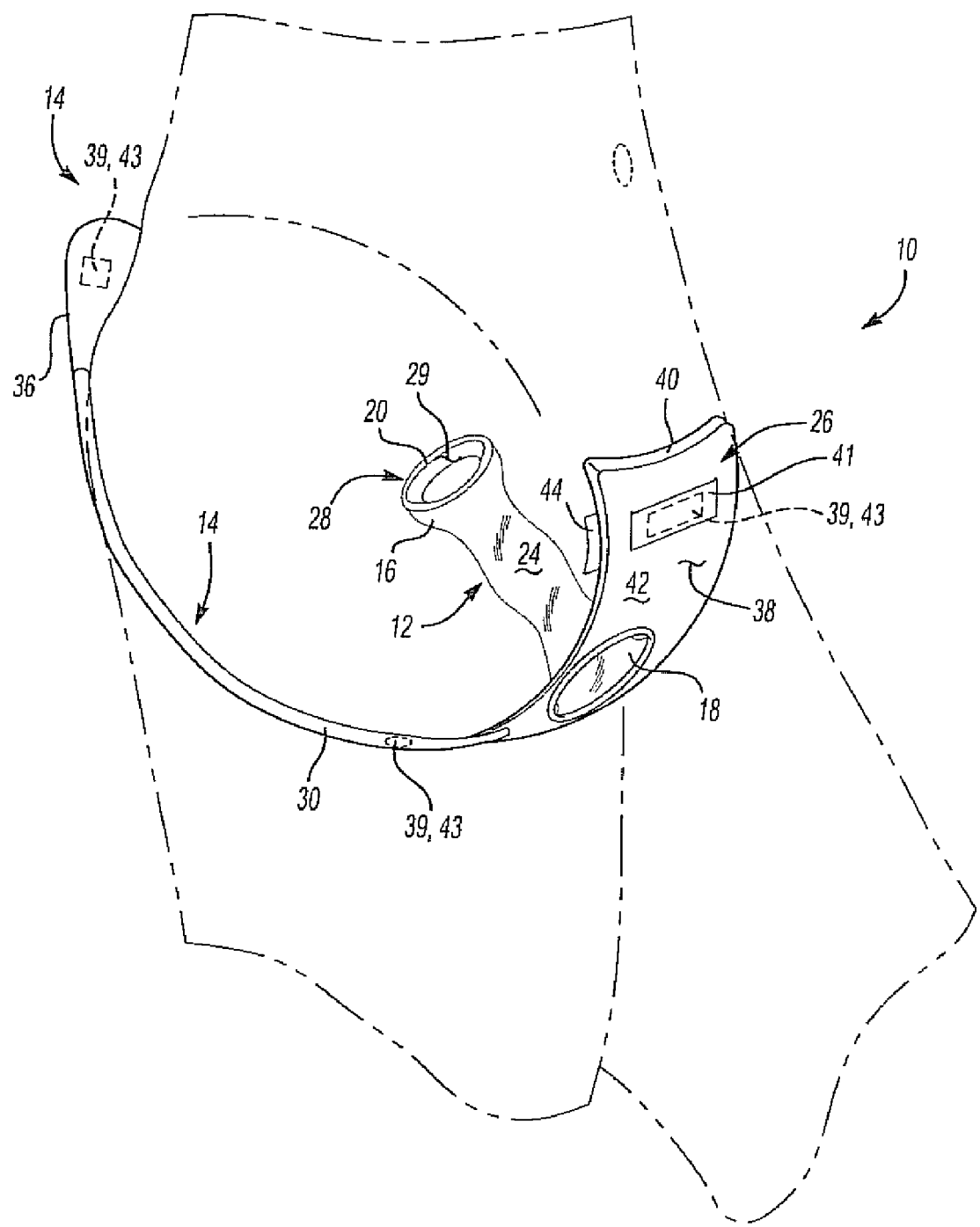
FIG. 4 is a perspective environmental view of still another embodiment of the improved condom of the present invention.

Referring now to FIG. 1, the improved condom 10 assembly may include a condom portion 12 and a harness 14. The condom portion 12 may include a pouch 16 having wall 24 that defines an open end 18 and a closed end 20 or at any point along on the wall of the condom pouch 16. The harness 14 may include one or more a strap(s) that may be secured to the open end 18 of the pouch 16 and may also be secured together at their opposite ends (as discussed below). The pouch 16 may be operable to be introduced into a user's vagina (see e.g., FIG. 20) to form a barrier to fluids between a penis and the vagina. The harness 14 portion of the assembly 10 may be worn by a user to assist in maintaining the pouch 16 in position during use.

Referring to FIGS. 1 and 2, the pouch 16 of the condom 12 may include a wall 24 that may be constructed of a continuous, water impermeable, flexible material such as latex, an organic material, or a polymer(s) or any other material known in the art. Indeed, it will be appreciated that any of the embodiments disclosed herein may be constructed of a water impermeable, flexible material such as latex, an organic material, or a polymer(s) or any other material known in the art.

A frame or rim 26 may be positioned on or within the wall 24 of the pouch 16 proximate the open end 18 and around the perimeter or a portion of the perineter thereof. The frame 26 may be detachable from the pouch 16 and may be constructed such that it is reusable or disposable. For example, the frame 26 may be constructed in two parts, a non-reusable frame integral to the pouch 16 and a reusable part that may be removably mounted to the non-reusable frame and designed to contain a condom accessory. Further, the frame 26 may be constructed in a variety of configurations including: as a roll of condom material, as a single flexible ring; as a single rigid ring; from two or more rigid or flexible elements disposed within pockets or piping surrounding the perimeter of the open end 18; or as a collar, collarette or flange (discussed below) that surrounds and extends away from the perimeter of the open end 18. The frame 26 may also be formed such that the open end 18 assumes a particular shape (e.g., a circle, triangle (V-shape), square, oval, rectangle, star, etc.). Accordingly, the frame 26 may be interchangeable, in addition to being reusable and/or disposable. The condom 10 of the present invention may also be constructed without a frame 26.

As shown in FIGS. 1-5, an anchoring device 28, such as a flexible disc or sponge 29, may be secured within the pouch 16, or external to the pouch 16, proximate the closed end 20 or at any point along on the wall of the condom pouch 16. Alternatively, a combination of anchoring devices 28 may be arranged with some device 28 positioned on the exterior of the pouch 16 and others positioned on the interior of the pouch 16. In operation, when the pouch 16 is inserted into a user's vagina, the anchoring device 28 may cause the wall 24 of the pouch 16 to press against the vaginal wall to better secure the pouch 16 in position and reduce the possibility of accidental removal of the pouch 16 during use. The anchoring device 28 may be constructed of a sponge or sponge-like material, a polymer, a non-porous material, a non-sponge material or any other material known in the art. Furthermore, the anchoring device 28 may be constructed in different shapes (circle, oval, square, rectangle, etc.) and sizes.

Figure 5:
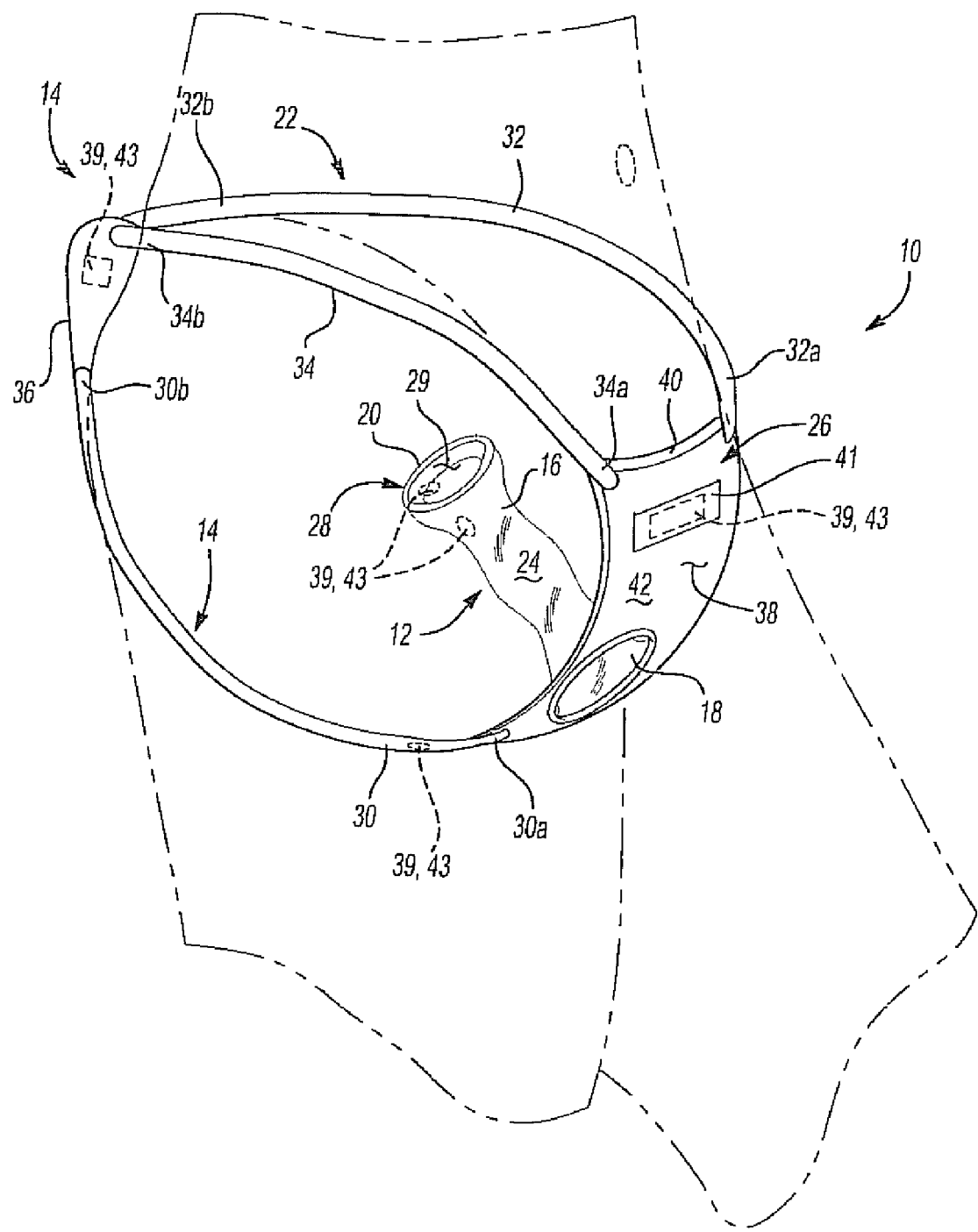
FIG. 5 is a perspective view of another embodiment of the improved condom of the present invention.

Referring to FIGS. 3-5, the harness 14 may include a center (or first) strap 30 and a pair (or a first and second) of side straps 32, 34. The center strap 30 may have an end 30a that may be secured to the open end 18 of the pouch 16. However, if the pouch 16 includes a frame 26, the end 30a of the center strap 30 may be secured to a portion of the frame 26. For example, where the frame 26 has a triangle (or V-shaped) shape (see e.g., FIG. 3), the end 30a of the center strap 30 may be secured to the frame 26 at an apex of one corner of the frame 26. The other end 30b of the center strap 30 may include a connecting member 36.

Still referring to FIGS. 3-5, the pair of side straps 32, 34 may each be secured at one end 32a, 34a to the open end 18 or, alternatively, the frame 26 of the open end 18 of the pouch 16. In the absence of a frame 26 the ends 30a, 32a, 34a of the straps 30, 32, 34 may be secured to the perimeter of the open end 18. Eyelets 35 may also be provided along the perimeter of the open end 18 or may be defined by the frame 26 to provide a point of attachment for the straps 30, 32, 34 to the condom portion 12. The opposite or other ends 32b, 34b of the side straps 32, 34 may be secured to or be formed integral with the other end 30b of the center strap 30 or the connecting member 36. Accordingly, the center strap 30 may be positioned between a user's legs and buttocks and the side straps 32, 34 may be positioned around a user's waist such that the harness 14 as described has the appearance of a G-string garment with the other ends 30b, 32b, 34b of the straps 30, 32, 34 being secured (as described above) in the region of the lower back of a user.

Referring to FIGS. 1-5, one or more of the straps 30, 32, 34 are formed such that it may be "spring loaded" or otherwise provide a resilient tension against a user when in use to further assist in securing the condom 10 in position during use. For example, the straps 30, 32, 34 may be formed or molded into an arc or U-shape using materials such a polymer or an insulated (or otherwise covered) wire of suitable gauge. Accordingly, it will be appreciated that the straps 30, 32, 34 may be constructed such that the straps 30, 32, 34 may be rigid, pliable, flexible or a combination thereof. The straps 30, 32, 34 may be constructed in a pre-stressed or shaped manner such that the straps conform (or hug) to particular body shapes (i.e., hips, waist, between the buttocks, etc.). The straps 30, 32, 34 may also be constructed of a glow-in-the-dark material or otherwise configured to glow in the dark (e.g., reflectors, lights, etc.). As will be further discussed below, the straps 30, 32, 34 may also be detachable.

As shown in FIGS. 4 and 5, the center strap 30 may be constructed as a pliable arc using a polymer material known in the art. As such, in operation, if the distance between the ends 30a, 30b of the strap 30 is insufficient to position the center strap 30 between a user's legs, the user may manually widen the strap 30. Thereafter, the user wears the harness 14 of the condom 10 as a G-string (see e.g., FIG. 5) and inserts the pouch 16 into the user's vagina. Once in position, the resilient nature of the strap 30 will push against the back (e.g., the "small-of-the-back") of the user in a clamping action to assist in holding the strap 30, and thus the condom 10, in position during intercourse.

As shown in FIGS. 1, 2 and 4, the assembly 10 may be constructed using only a single strap. For example, the center strap 30 may be a rigid, pliable, flexible or combination member that may be constructed such that it extends from the open end 18 of the condom portion 12, between the user's legs and buttocks and pushes against the user's back in a clamping action. Further, the side straps 32, 34, if present, may be constructed such that those straps 32, 34 are detachable (as shown in FIG. 3) from the condom portion 12. As shown in FIG. 3, the center strap 30 may also be designed to be detachable such that the entire harness 14 assembly may be reused. Accordingly, the entire harness 14 may be constructed as a separate unit apart from and connectable to the pouch 16 (or the frame 26, as described below). Specifically, in such an embodiment, a releasable clip 58 37 (or like clasping device) may be disposed at the end 30a, 32a, 34a of each strap 30, 32, 34. The clip 58(s) 37 are operable to engage the frame 26 (or, alternatively the wall 24 where there is no frame 26) of open end 18 of the pouch 16.

Referring to FIGS. 1 and 2, to provide additional comfort to the user, the connecting member 36 at the other end 30b of the strap 30 may be constructed in a triangular form, enclosed circle or oval, or as a contour shaped body conforming shape. The connecting member 36 functions to distribute the clamping action of the strap(s) 30, (32, 34) to the user's hips or back and also provides greater comfort for the user.

As shown in FIGS. 4 and 5, the condom 10 assembly may also include one or more condom accessories. Specifically, condom 10 assembly may include a condom accessory that in one embodiment may be electronically charged to pulsate or vibrate (or oscillate) causing the condom portion 12 to do the same (and thereby transmit a vibration (or oscillation) or other sensation to the user or the user's partner) by virtue of being connected to, for example, the straps 30, 32, 34 or any other part of the condom 10. More particularly, in any of the embodiments disclosed therein the condom accessory(s) may include one or more condom accessories (e.g., a vibration or pulsing device 39) that may be positioned on or within a variety of positions, including but not limited to, the condom portion 12, the harness 14, the anchor 18, on or in the wall 24 of pouch 16 of the condom 12, at any point along one or more of the straps 30, 32, 34, at the connection point of the straps 30, 32, 34, on, in or in proximity to the eyelets 35, on a clip 58(s) 37, on or in the connecting member 36, in or on the anchoring device 28 and/or (as described below) on the frame 26, within a pillow or cushion (as described below), within the frame, rolled within the condom portion 12, in a cavity defined in condom portion 12, the harness 14, the anchor 18, wall 24 or the frame.

By way of example, when positioned on a strap 30, 32, 34 the vibration or pulsing device 39 may induce or transmit a pulsation and/or vibration to the strap 30, 32, 34 that may then be communicated to the condom portion 12 (including the frame 26 thereof). The vibration or pulsing devices 39 (or any condom accessories recited herein) may be controlled by microchip or integrated circuitry, and may be activated by a manual switch (e.g., a toggle switch), pressure switch (e.g., a membrane switch) or a thermal switch or any other switch known in the art. For example, the vibration or pulsing devices 39 may be powered using e.g., an on-chip, micro-battery, or like commercially available kinetic motion technology, a hearing aid battery or similar size battery, mounted on in proximity to the device 39 or the like. An example of a kinetic motion power generating source was disclosed in U.S. Pat. Nos. 5,822,278 and 6,154,422 to the Seiko Epson Corporation, the disclosures of which are incorporated by reference herein. As an alternative (or in addition) to the vibration or pulsing device 39, the condom accessory may also include or comprise a chemical or electronic heating element 43, such as a heater chip, thin film heating element, micro-fibers integrated into one or more elements/structures of the condom 10 assembly or a known exothermic agent or similar known chemical agent that create the sensation of heat. One or more heating elements 43 also may be positioned on the condom 10 along with, or in place of, a vibration or pulsing device 39 at any point where a vibration or pulsing devices 39 might also be positioned as described above. Further, the heating element 43 may be powered (if necessary) using the same or similar means described above for use in connection with the vibration or pulsing devices 39. The motion and/or heat of the condom 10 assembly thus provides added stimulation to the female wearer of the condom, as the vibration and/or heating sensation may be felt on the female sex organs.

Still referring to FIGS. 4 and 5, alternatively, or additionally, the vibration or pulsing device 39 may be positioned on or connect to the frame 26. For example, the device 39 may be disposed within a pocket 41 on the frame 26 or that may be disposed within the wall 24 or may be otherwise mounted in any manner described above or as will be described below. If the frame 26 is a flange or collar, the pouch 16 may be disposed on the side of the frame 26 that faces the user or the side of the frame 26 that faces away from the user.

Referring to FIGS. 3-5, the open end 18 of the pouch 16 may include a continuous flange member 38. As set forth above, the flange 38 may be constructed such that it extends outwardly from the open end 18 of the pouch 16 between one and four inches, depending on the needs of the user. The flange 38 may also function as the frame 26 (see e.g., FIG. 3). The flange 38 has an interior surface 40 that faces toward the user when the condom 10 is in use and an exterior surface 42 that faces away from the user when the condom 10 is in use. The flange 38 extends outwardly around the perimeter of the open end 18 of the pouch 16 and may be constructed of a flexible or nonflexible and elastic or non-elastic material. The flange 38 may also be impermeable to liquid.

Referring now to FIG. 4, a pad 44 may be positioned on the interior surface 40 (i.e., so that it contacts the user's skin), exterior surface 42 or both surfaces 40, 42 of the flange 38 (frame 26). The pad 44 may also extend completely or partially around the entire circumference of the open end 18 of the pouch 16. The pad 44 may be a sponge or sponge-like material. The pad 44 may also be impregnated or otherwise coated with a spermicide, an antibacterial agent, a microbiocidal agent, a scent agent or a flavorant agent. For example, a flavorant agent may be released into the interior of the condom 10 as a means of promoting oral sexual stimulation. According, it will also be appreciated that the condom 10 may thus function as an oral dam.

Referring now to FIGS. 6-20, there are shown additional embodiments of an improved condom 10 wherein (as described above) one or more additional condom accessories, including fluids, may be fixed or positioned on or to the condom 10 using a variety of methods. For example, as mentioned above, the condom accessory(ies) may be positioned on or within the condom portion 12, the harness 14, the anchor 18 or the frame 26. Further, methods of positioning the condom accessory(ies) include rolling the accessory(ies) into the condom portion 12, adhering the accessory(ies) to the surface of the wall 24 of the condom portion 12, to the harness 14, to the anchor 18 or to the frame, embedding the accessory (ies) within the condom portion 12, the harness 14, the anchor 18 or the frame 26, and placing the accessory(ies) in a pillow or in a space or pocket 50 defined in the condom portion 12, the harness 14, the anchor 18 or the frame 26. The condom accessories described herein may be designed for a single use and to be disposable. However, it will be appreciated that the condom accessories may also be designed for multiple uses.

Figure 6:
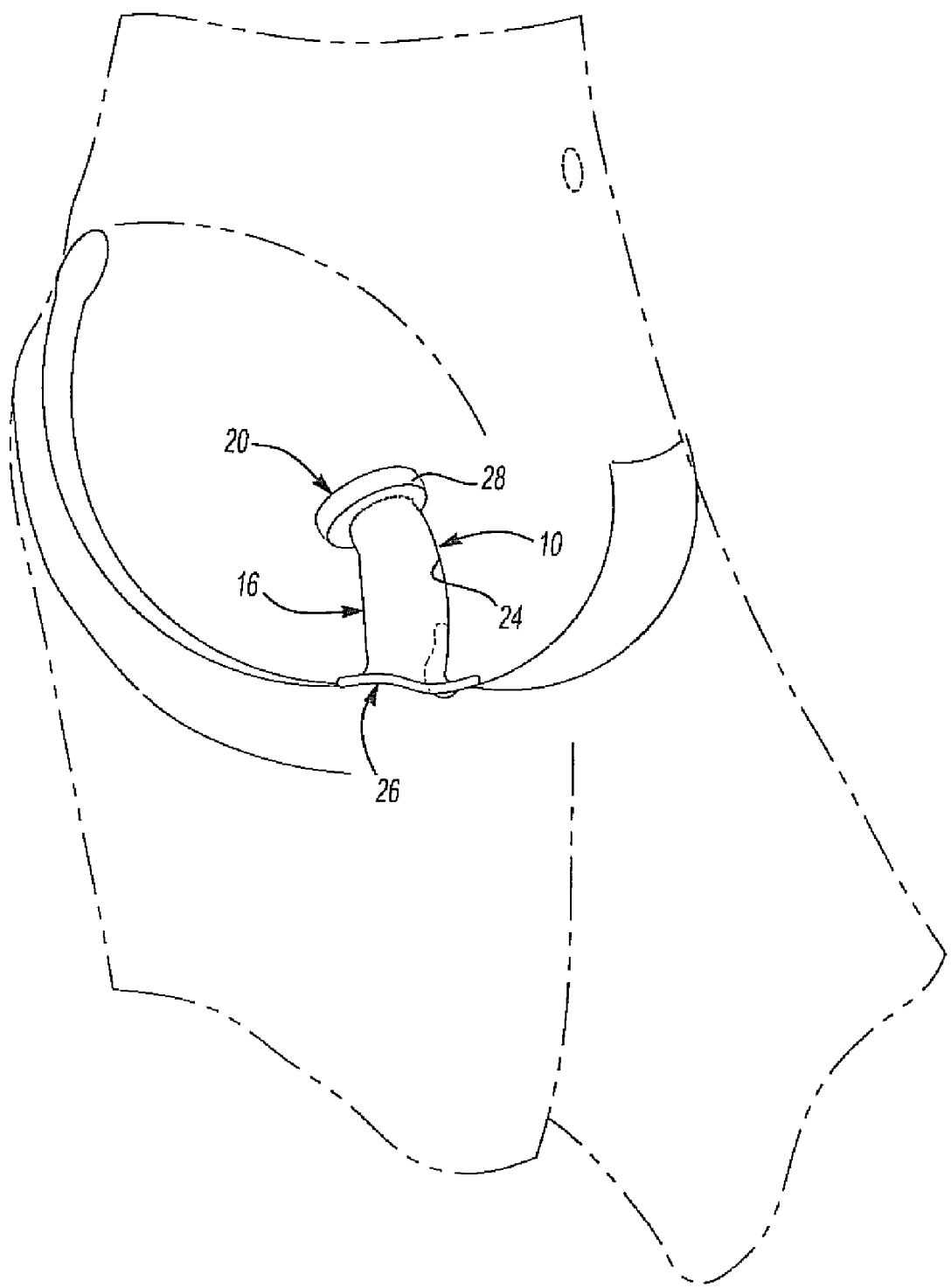
FIG. 6 is a perspective view of another embodiment of an improved condom that includes a space or pocket for containing a condom accessory.
Figure 9:
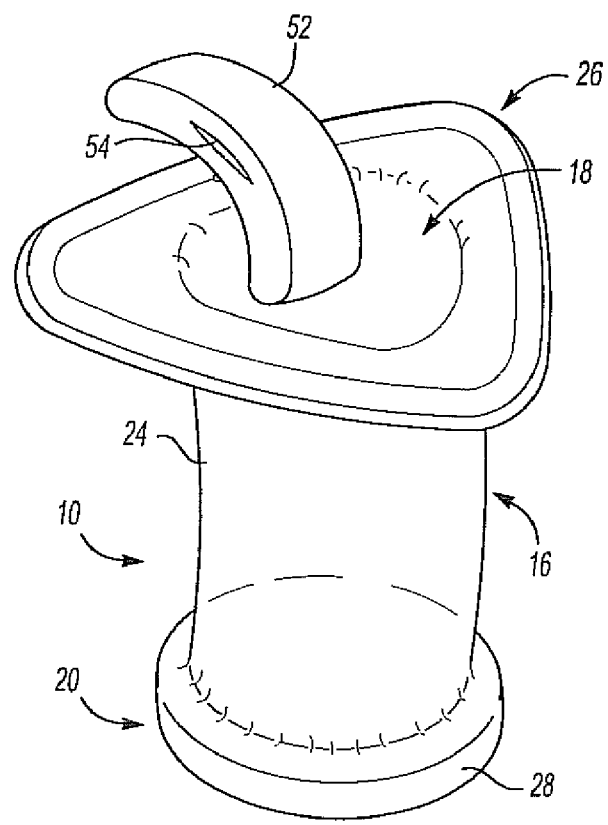
FIG. 9 is a perspective view of an embodiment of an improved condom having a pillow positioned on the frame of the condom that includes an opening to permit the insertion of a condom accessory.

As previously mentioned, the condom 10, particularly the pouch 16, of the condom portion 12, of the additional embodiments may be constructed of a water impermeable, flexible material such as latex, organic materials, or a polymer(s) or any other material known in the art. Further, the frame 26 of the condom 10 may be constructed of a molded polymer(s) using blow or injection molding, extrusion methods, or similar molding technology. Further, as best shown in FIG. 6, it will be appreciated that the embodiments shown in FIGS. 6-20 of the condom 10 may be constructed with or without a harness 14.

Referring now to FIGS. 7-10, the condom accessory may be formed as a flexible walled container. In this regard, the spaces or pockets 50 may be formed as a cushion or pillow 52 having an open end (e.g., a tube of latex having a closed end) (not shown). The interior of the cushion or pillow 52 may include padding 53. Additionally, one or more condom accessories may be positioned within the cushion or pillow through the open end. Thereafter, the cushion or pillow 52 may be secured to the condom portion 12 or the frame 26 thereof by, for example, rolling the open end of the cushion or pillow 52 into the frame 26/open end of the condom 10 (to thereby enclose the condom accessory(ies) in the cushion or pillow) or by fixing the cushion or pillow 52 to the condom portion 12 with a non-toxic adhesive. Additionally, or alternatively, following the insertion of a condom accessory, the cushion or pillow 52 may be sealed. The cushion or pillow 52 may then be secured by molding, adhesives, rolling or the like, to the frame 26 of the condom portion 12 at any point along the body of cushion or pillow 52. For example, as shown in FIGS. 7-10, the cushion or pillow 52 may be secured to the frame 26 at a mid-point of the cushion or pillow 52. Alternatively, the cushion or pillow 52 may be secured to the frame 26 along an end or edge of the cushion or pillow. Further, the cushion or pillow 52 shown in FIGS. 7-10 may be positioned at any point along the frame 26 or the pouch 16 and be constructed in a variety of shapes and sizes. Accordingly, it will be appreciated that the placement and the dimensions of the cushion or pillow 52 are not limited to that specifically shown in the drawings.

Figure 10:
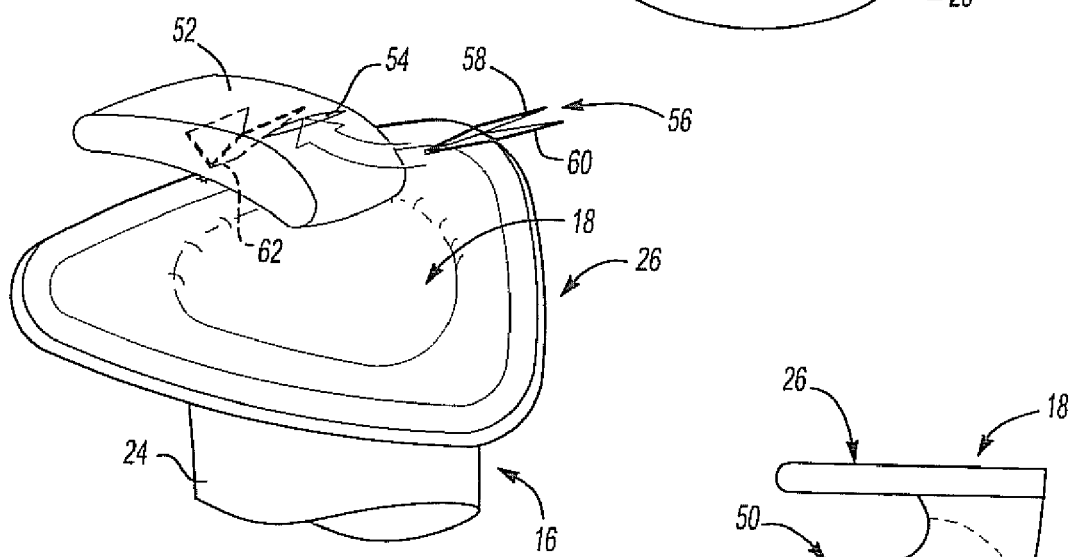
FIG. 10 is a perspective view of the embodiment of an improved condom shown in FIG. 9 showing a condom accessory positioned in the pillow.

Referring now to FIG. 10, the cushion or pillow 52 may include an opening 54 to permit a user to insert, or partially insert, another condom accessory (aside from the pillow itself, which should also be considered a condom accessory) into the cushion or pillow 52 prior to use of the condom 10. For example, the condom accessory may further include a pillow clip 56. The pillow clip 56 may include a V-shape that may be formed by the pillow clip 56 having a first 58 and a second 60 panel that may be joined along a common edge 62. A shown, the first 58 and second 60 panel may be trapezoidal in shape (and joined along the shorter of the two parallel sides). However, other shapes may also be adopted for the construction of the pillow clip 56.

Still referring to FIG. 10, the first 58 and second 60 panel may be folded toward each other such that the angle between the panels 58, 60 is between 80 and 120 degrees. However, a larger (e.g., between 120-179 degrees) or a narrower angle (e.g., 50-80 degrees) may also be used. It will also be appreciated that at an angle of 180 degrees the first 58 and second 60 panel may be fully extended away from each other in the same plane, and at an angle of zero degrees or substantially zero degrees a surface of the first panel 58 may be contacting a surface of the second panel 60. The pillow clip 56 may be formed of as a semi-rigid device using commercially available polymers and manufacturing techniques. However, the pillow clip 56 may also be constructed as a rigid device or may be highly flexible as may be required to meet the needs of a particular user.

Still referring to FIG. 10, the common edge 62 of the pillow clip 56 may be oriented such that it faces or points toward the exterior of the wall 24 of the condom portion 12. As such, during use the pillow clip 56 may form a ridge or protrusion from the wall 24 (or frame or sponge, or wherever else the clip 56 is positioned) of the condom portion 12 that may create friction (or additional friction) between the exterior surface of the condom portion 12 and the skin of the wearer. For example, if condom 10 is properly positioned, the ridge created by the pillow clip 56 may rub against, and thereby physically stimulate, thereby enhance the male or female wearer's physical experience.

Figure 11:
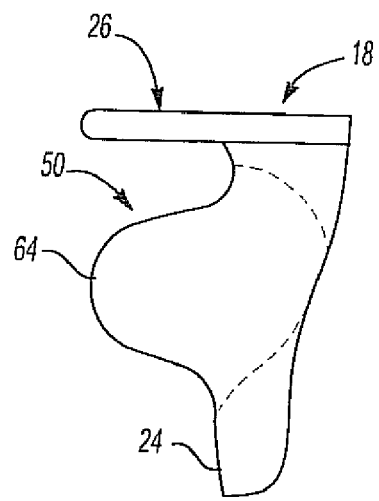
FIG. 11 is a partial planar side view of an embodiment of an improved condom showing the pocket or bulge defined in a wall of the condom.

Referring now to FIGS. 11-17, spaces or pockets 50 may further be defined along or integral with an interior or exterior wall 24 of the body of the condom portion 12. More specifically, and as best shown in FIG. 11, the one or more spaces or pockets 50 may include a pocket or bulge 64 of material formed in the wall 24 of the pouch 16. Additionally, or alternatively, the spaces or pockets 50 may be constructed as a closed or sealed space form in the wall of the pouch by, for example, overlaying the wall 24 of the condom portion 12 with material 66 to create the spaces or pockets 50. Alternatively, the spaces or pockets 50 may be created though modified latex dipping techniques, or polymer molding.

Referring now to FIG. 11, it will be appreciated that the molding of a pocket or space 50 in or on the wall 24 of the pouch 16 may provide the pouch 16 with an asymmetrical shape. In use, such a pocket or bulge 64 may promote the touching or gripping of the vaginal wall by the pouch 16 of the condom portion 12 in a manner that creates a degree of frictional adhesion between the wall 24 of the pouch 16 and the vaginal wall. This frictional adhesion may result in greater pleasure for the wearer. Furthermore, a condom accessory may be positioned in and encased by the pocket or bulge. The wall 24 of the condom portion 12 may then be rolled upward from the open end 18 to secure the condom accessory in position in the pocket or bulge 64.

Still referring to FIGS. 11-17, and as best shown in FIG. 12, a condom accessory may be positioned in the spaces or pockets 50. As already discussed above, the condom accessory may be any manner of condom accessory including a vibration device, a fluid or gel 68 (FIG. 14), a light and/or sound emitting device 70 (FIG. 15) or a pad 72 (FIG. 12). The condom accessory may also include a solid form device, such as a solid tablet (FIG. 11), or a tablet capable of dissolving during use of the condom. The condom accessory may include a solid molded frame 74 (FIG. 19). The condom accessory may also include or be coated with an agent (e.g., a spermicide, antibacterial or microbiocidal agent) and may be a scented or flavored fluid, gel or apparatus. Further, the fluid or gels may include a desensitizing gel or chemical that may be released into the interior of the condom to inhibit or otherwise postpone male ejaculation. The condom accessories may be constructed to be deposable or reusable. Furthermore, the condom may be constructed so that the user may interchange the condom accessories to meet his or her needs.

Still referring to FIG. 12, the condom accessory may also include a pad 72. More specifically, the pad 72 may be an absorbent pad that may operate to absorb natural and artificial fluids. As mentioned above, the pad 72 may be coated with a spermicide and may also include one or more textured surfaces.

Where the pad 72 includes a textured surface (or is otherwise large enough to make contact with the user during use, it may be desirable to construct the pad 72 so that it is semi-rigid along at least the portion of the pad 72 having the textured surface. It will be appreciated that the textured surface of the pad 72 may serve to stimulate the user in a manner similar to that described supra in connection with the pillow clip 54.

Additionally, or alternatively, the pad 72 may be constructed such that all or a portion of the pad 72 is highly flexible and sponge-like such that a high degree of comfort may be transmitted to the wearer. As mentioned above, the pad 72 may be impregnated with a condom accessory in the form of a fluid or gel. Further, the pad 72 may be positioned on or in the condom portion 12, the anchor 18, the frame 26 or any other portion of the condom 10 in a manner such that the pad is impacted (by, for example a male penis) or otherwise frictionally engaged during use. It will be appreciated that the impacting of the pad 72 during use will promote release or activation of the condom accessory.

Referring now to FIG. 13, as mentioned above, the spaces or pockets 50 may include an opening 74 that would permit a user to insert a condom accessory into the spaces or pockets 50 prior to use. However, the opening 76 may also be formed such that it permits the release of the condom accessory or the intake of human fluids. For example, as shown in FIG. 13, the opening 76 defined in the cavity or pillow 50 may be used to permit the release of a scented, unscented, or warming gel or fluid that is contained in the spaces or pockets 50 prior to use. Alternatively, where the condom accessory is a pad 72, the opening may permit the pad 72 to absorb human fluids and/or introduce, e.g., a predetermined agent. Further as mentioned above, the pad may be positioned on the frame 26 so that it contacts the user's skin. The pad 72 may be mounted on the frame so that it extends completely or partially around the frame between the condom and the user's skin. As such, it will be appreciated that the pad may be arranged in such a manner that is may absorb menstrual and other human fluids.

Referring now to FIG. 14, the condom accessory may include a fluid or gel 68.

Referring now to FIG. 15, the condom accessory may include a light and/or sound emitting device 70. More specifically, the condom accessory may include a light and sound emitting device 70 that includes one or more light emitting diodes (LEDs) 78, a memory means (e.g., EPROM or Flash memory), a sound emitting means 80 (e.g., a speaker) in electrical communication with the memory means, a pressure-sensitive switch 82 that may activate the LEDs 78 and the memory means and a power source (e.g., a battery) in electrical communication with the LEDs 78, the memory means and the sound emitting means. The memory means may include preprogrammed data relating to one or more sounds (i.e., music and/or sound effects) and also data relating to patterns for selectively activating the LEDs 78. The emission of sound from the sound emitting means 80 may also be coordinated with the activation of the LEDs 78 to create an overall pleasing light and sound stimulation effect.

Referring now to FIGS. 16 and 17, the spaces or pockets 50 may include one or more micro-apertures 84 defined in the wall 24 of the spaces or pockets 50 that may be biased into a closed state by the inherent tension of the material of the condom wall 24. More specifically, it will be appreciated that absent the influence of an external pressure (such as hand pressure or pressure created during use of the condom), the pressure of the fluid in the spaces or pockets 50 may not be sufficient to overcome the inherent tension of the material of the condom wall 24, open the micro-apertures 84, and communicated fluid to the surface(s) of the condom portion 12. However, pressing on the spaces or pockets 50 or making normal use of the condom 10 may result the addition of sufficient pressure to overcome the tension of the material of the condom wall 24 and result in fluid being communicated to the surface(s). The use of the micro-apertures 84 may also permit a gradual release of a fluid or gel 68 from within the spaces or pockets 50 or permit the gradual uptake of fluid from the environment.

Figure 20:
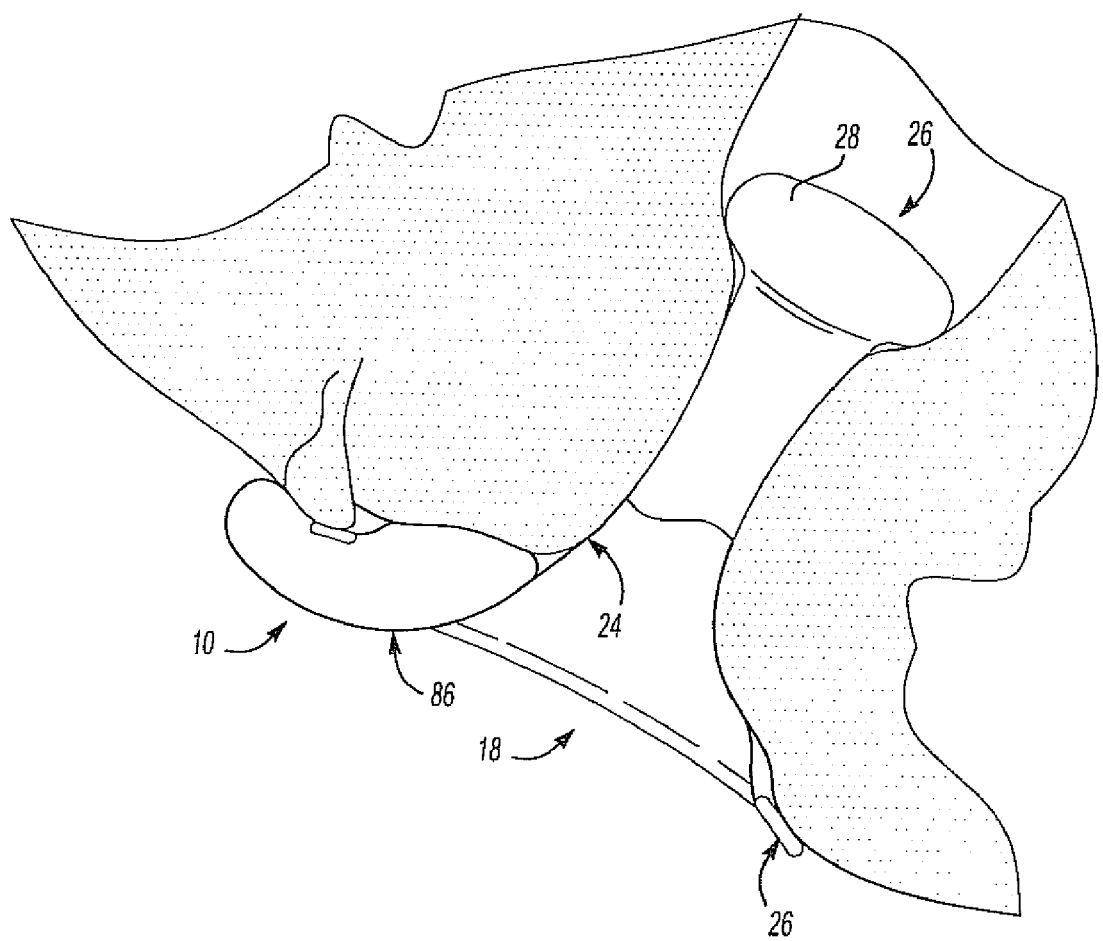
FIG. 20 is an environmental side view showing the improved condom of FIG. 18 or FIG. 19 in use.

Referring now to FIGS. 18-20, the spaces or pockets 50 may also be defined in the frame 26 of the condom 10. More specifically, the spaces or pockets 50 may include a chamber 86 molded (through blow or injection molding or the like) integral with the frame 26 of the condom 10. As shown in FIG. 18, the wall of the chamber 86 may include a lattice structure 86 or similar construction such that the chamber 86 is at least partially open to the environment. Alternatively, the wall of the chamber 86 may be completely enclosed or, as described above, include one or more opening or micro-apertures 84. Further, any of the condom accessories mentioned above may be positioned in the chamber through an opening 54 defined in a wall of the chamber. The opening 54 may be of a fixed dimension or (as is the case with the micro-apertures) may be constructed of an elastic material such that it is normally biased in a closed position. Additionally, as best shown in FIG. 19, the spaces or pockets 50 may be a solid form that may or may not encase a condom accessory.

Referring now to FIG. 20, the spaces or pockets 50 (here the chamber 86 variety thereof) may be positioned or arranged on the condom 10 (including the frame 26 thereof) such that the spaces or pockets 50 may stimulate the female clitoris. Additionally, or alternative, the spaces or pockets 50 may be positioned or arranged on the condom such that increase sensation is transmitted to the male penis.

Having thus described my invention, various other embodiments will become apparent to those having skill in the art that do not depart from the scope of the claims or equivalents thereof.

I claim:

1. An improved condom apparatus comprising:
    a female condom having a pouch having a wall and a frame, the wall defining an open end and a closed end of the pouch and the frame being positioned proximate the open end of the pouch, the frame defining a space or pocket;
    an anchoring device secured within the pouch proximate the closed end; and
    a condom accessory positioned in the space or pocket of the frame.

2. The improved condom apparatus of claim 1 wherein the condom accessory comprises a pad impregnated with a fluid or gel, such that during use impacting the pad promotes release or activation of the fluid or gel.

3. The improved condom apparatus of claim 2, wherein the frame includes a lattice that defines the space or pocket.

4. The improved condom apparatus of claim 1, wherein the condom accessory comprises a switch operable to activate the condom accessory.

5. The improved condom accessory of claim 4, wherein the switch of the condom accessory is selected from a group consisting of a toggle switch, a pressure switch and a thermal switch.

6. The improved condom apparatus of claim 1, wherein the condom accessory comprises a vibration device.

7. The improved condom apparatus of claim 1, wherein the condom accessory comprises a pillow clip.

8. The improved condom apparatus of claim 1, wherein the condom accessory comprises a light and sound emitting device.

* * * * *